United States Patent
Baron

(10) Patent No.: US 6,741,083 B2
(45) Date of Patent: May 25, 2004

(54) OSCILLATING DEVICE FOR THE DETERMINATION OF THE PURITY OF SINGLE OR MULTI-COMPONENT LIQUIDS FROM THEIR DIELECTRIC PERMITTIVITY, IN A CONTINUOUS WAY AND THROUGH FREQUENCY CHANGES IN THE STATIC PERMITTIVITY REGION AND AN ASSOCIATED MEASUREMENT PROCEDURE

(76) Inventor: Maximo Baron, Santa Fe 3586 7th "B", Buenos Aires (AR), 1425

( * ) Notice: Subject to any disclaimer, the term of this patent is extended or adjusted under 35 U.S.C. 154(b) by 288 days.

(21) Appl. No.: 09/985,989

(22) Filed: Nov. 7, 2001

(65) Prior Publication Data

US 2003/0122555 A1 Jul. 3, 2003

(30) Foreign Application Priority Data

Nov. 9, 2000 (AR) .................................. P00 01 05900

(51) Int. Cl.$^7$ ................ G01R 27/26; G01N 27/60
(52) U.S. Cl. ............... 324/668; 324/674; 324/685; 324/689; 324/453
(58) Field of Search ................. 324/668, 674, 324/681, 689, 453; 340/618, 620; 73/861.14, 61.61

(56) References Cited

U.S. PATENT DOCUMENTS 4,736,156 A * 4/1988 Benson et al. ............... 324/668
4,782,282 A * 11/1988 Bachman ..................... 324/668

* cited by examiner

Primary Examiner—Anjan K. Deb

(57) ABSTRACT

An oscillating device to determine the purity of single or multi-component liquids on the basis of their dielectric permittivity, in a continuous procedure through the frequency change in the static permittivity region and with strict temperature control. The oscillator is connected to a standard thermoregulated measuring cell, a frequency meter and a power source. The improved characteristic is that the circuit does not contain the usual micrometer and standard capacitors and that it has a previously determined inductance to improve measurement conditions. In this manner, and operating in the region of static frequencies to avoid relaxation phenomena, a continuous measurement is achieved with a high degree of precision that had never been previously obtained. A measurement procedure is also disclosed that is carried out with the device.

3 Claims, 5 Drawing Sheets

OSCILLATING DEVICE FOR THE DETERMINATION OF THE PURITY OF SINGLE OR MULTI-COMPONENT LIQUIDS FROM THEIR DIELECTRIC PERMITTIVITY, IN A CONTINUOUS WAY AND THROUGH FREQUENCY CHANGES IN THE STATIC PERMITTIVITY REGION AND AN ASSOCIATED MEASUREMENT PROCEDURE

BACKGROUND OF THE INVENTION

1. Field of the Invention

The present invention refers to an oscillating device to determine the purity of single or multi-component liquids, on the basis of their dielectric permittivity, in a continuous form under strict temperature control and through frequency changes in the static permittivity region and to the associated measurement procedure.

More precisely it refers to an oscillator to determine in a continuous fashion the degree of coincidence of the global composition of a liquid, either single or as a mixture of two or more components with a previously established standard, by means of a high sensitivity oscillating circuit containing a temperature controlled capacitance cell.

For this purpose it is based on dielectric permittivity measurements (previously called dielectric constant, until this denomination was changed by the International Union of Single and Applied Chemistry, as stated in the $2^{nd}$ Edition of Quantities, Units and Symbols in Physical Chemistry, published in 1993) taking into account that it is one of the physical properties that is most sensitive to the composition of liquids.

2. Brief Description of the Prior Art

The verification and continuous following of the global composition of a liquid, either single or multi-component, during production processes, at the end of it and before its use in the final destination, is one of the most important technologic problems. Especially because, very frequently, a detailed knowledge of the composition is not needed and it is only important whether or not it is within the requirements of a previously, in general physical, established standard.

Under these conditions devices that require the taking of a sample and its later analysis in a place, near or far; from the production line, are not adequate because they imply either the interruption of the process until the answer is available or the risk that an out of specification product continues in the process or is used in its final application.

This is the typical case of solvents, liquid fuels, liquid lubricants, transformer liquids and isolating liquids in general.

As is known, the permittivity of any given substance is obtained from measurements in capacitors comparing their capacitance values in vacuum and containing the substance to be examined through the following equality:

$$\in = C_f/C_e$$

wherein $\in$ is the permittivity, $C_f$, $C_e$ respectively the capacitance of the filled and empty capacitor. Actually the latter value corresponds to the air filled capacitor since for all practical purposes there is no substantial difference between the vacuum permittivity, taken as unity and that of atmospheric air, which under normal conditions of temperature and pressure is $\in = 1,00059$.

To determine these capacitances RLC, LC or RC oscillating circuits are used, among other devices, having oscillating frequencies that run from fractions of Hertz to Gigaherts, that are clearly in the microwave region.

Depending on the frequency measuring range used for permittivity determination, the latter can be divided into two well differentiated classes: static and complex permittivities. Static permittivity is determined at frequencies never exceeding 5 MHz, although in general operations are carried out below 1 MHz. These values depend on the size of the molecules of the substance being examined because this is what determines their ability to "follow" the oscillations of the applied electric field. In other words, plotting permittivity as a function of frequency, the first region (0 Hz to 5 MHz) will be represented by a straight line parallel to the abscissa (frequency) axis. Once this limit is surpassed the permittivity becomes complex being the result of the sum of two components, one real and the other imaginary, because the molecules oscillation frequency suffers a progressive phase shift with regards to the oscillation frequency of the electric field. This is the so called relaxation phenomenon that is in turn the fundamental characteristic of this region of the frequency spectrum and its amplitude changes with the size of the molecules involved.

Both the theory and the oscillators used in the determination of both types of permittivities are completely different. In general the former (static permittivity) are far more accessible and simpler than the latter (complex permittivity). In any case both have very important fields of application that vary depending on the nature of the problems to be solved.

The most important advantage of the static permittivity determinations are: their evident independence from the oscillation frequency with the consequent ease to reproduce measured values, the low influence of residual capacitances (resulting from cables, connections and eventual empty spaces in the capacitor) and the precision and high sensitivity that can be obtained with the modem circuits based on integrated electronic components. This is not the case of the complex permittivity because determinations of similar quality have not been achieved.

This latter situation is the result of the well known fact that while with complex permittivity and relaxation, determinations in general do not provide results with better than the second decimal, in the case of static permittivity the fourth decimal can be reached without difficulties.

Therefore static permittivity becomes an ideal parameter to establish macroscopic characteristics of substances (especially fluids) and compare them with preestablished appropriate standards.

Presently known procedures, that provide these results, are based on electronic circuits of the RLC type wherein the capacitance (C) is formed by a number of capacitors in parallel: a measuring cell, a standard capacitor and a micrometric capacitor. This is quite adequate for discontinuous measurements and although the sensitivity and precision are acceptable, the standard and micrometric capacitor, as mechanical devices, are a source of important difficulties, such as: mechanical backlash, sensitivity to ambient temperature, complexity in the connections that require a rigidity not easy to achieve (any movement during the measuring procedure causes appreciable changes in the results), the impossibility to develop any type of automatic processing or continuous recording, preventing the use of computers and the need to make several capacitance measurements before the desired permittivity can be calculated.

Regarding this latter mentioned fact it is necessary to take into account and review briefly the manner in which the measurements are carried out, in what can be called the traditional way, that is using capacitors through the so called substitution method.

As stated above an oscillator is used the capacity of which is formed by three capacitors in parallel:

- a measuring cell
- a standard capacitor, that can be any one available in the market as for instance of the General Radio brand (although any other one of similar characteristics is equally acceptable). These capacitors have a range that covers from 150 to 1000 picoFarads (pF) and a sensitivity of 0.5 pF.
- a micrometric capacitor, formed by a micrometric screw, of the caliper type, with a 3 to 4 cm stem that can be introduced in a bronze cylinder the inside diameter of which is machined so that with the outer diameter of the stem a 2 pF capacitor is obtained for a length of 20 divisions of the screw.

In general the substitution method comprises the steps of:
- determining the capacitance of the circuit without the three mentioned capacitors,
- determining the capacitance of the empty cell, subtracting from it the value of the so called residual capacitance, that corresponds to that part of the cell that is not in contact with the liquid to be examined and all the connections that lead to the oscillator,
- determining the capacity of the cell once the dielectric has been introduced.

The instruments used comprise two oscillators. One (fixed) is based on a crystal of oscillating frequency chosen between 100 and 500 kHz, depending on what is available regarding stability. To this effect the low frequency ones (100 kHz) are preferred because they are far less sensitive to changes in the at ambient temperature and therefore require less space because they do not need a heating chamber, as is the case with those of higher frequency (500 kHz). The other oscillator is variable because its oscillating frequency depends mainly on the capacitance of the already mentioned battery of three parallel capacitors. The procedure essentially requires that the variable oscillator is made to oscillate at a frequency that is very close to that of the fixed oscillator so that the difference in frequency is a whole number that can then be compared to any well known and very stable frequency signal.

Although this may sound extremely complex it is actually quite simple because the difference that is looked for between the two frequencies is of 50 or 60 Hz, depending of the frequency available in the utility power lines, or a multiple of this value (100 or 120, 150 or 180, etc). This signal can be supplied to the horizontal input of an oscilloscope (CRO), the vertical input of which is connected to the utilities power line (that may be 50 or 60 Hz). The input can be exactly the reverse because in both cases the result will be identical since a Lissajous figure is obtained the form of which varies depending on the multiplicity of the variable oscillator signal. If both are 50 (or 60) Hz signals the resulting figure is a circle that will be as motionless as close as the two frequency values are. If the difference of the to oscillators is of 100 (120) Hz the resulting figure corresponds to the 2:1 ratio. This one is preferred because it is much easier to observe.

The measuring procedure then comprises the following steps:
- set the scale of the micrometric capacitor to zero
- disconnect the battery of capacitors
- determine the capacity of the oscillator setting the standard capacitor dial at the full capacity value that leads to the closest chosen Lissajous figure. For this purpose the marks on both the fixed and movable dial are set perfectly in line. The same mode of approach must always be followed to avoid undesirable mechanical backlash. Regardless of the width of the two lines one edge of each is chosen for all the measurements. Otherwise substantial changes will be found in successive readings. The micrometric screw is then used to adjust the capacity until the desired Lissajous figure remains absolutely still. In this way values within one thousandth of pF can be obtained. The second capacity reading is subtracted from the first one and from this value the residual capacitance is subtracted, giving the capacitance of the empty cell. Strictly speaking this is the capacitance of that part of the cell that will contain the dielectric material to be examined. The residual capacitance is obtained as indicated later.
- As a matter of fact what has been done with this operation was to substitute the capacitance of the cell using the standard and micrometric capacitors. Hence the name of substitution method.
- now the liquid to be examined is introduced into the cell, filling is controlled through an overflow, and the capacitance is measured in the same manner as with the empty cell,
- the cell is now disconnected and the capacitance of the oscillator is measured again. This value must not differ more than 0.03 pF, because this is the experimentally determined upper limit value that will lead to permittivity values with an error smaller that 0.0001 units, in other words with four exact decimal figures.
- the capacitance measured for the filled cell is then subtracted from the value of the final oscillator capacitance and from this difference the residual capacitance is then subtracted,
- the capacitance of the filled cell ($C_f$) is divided by the capacitance of the empty cell ($C_e$) and the value of the permittivity ($\in$) is finally obtained,
- the residual capacitance is determined in a totally similar fashion with the sole exception that a liquid of exactly known permittivity is used and the capacitance value is obtained form the equation wherein the $\in$ of a standard liquid is used as data. For this purpose benzene or carbon tetrachloride can serve because both liquids are easily purified to values of 100% purity if kept under a pure and dry nitrogen blanket.

It has become evident in the former description that there is a high number of mechanical operations to be performed, with the consequent accumulation of mechanical backlash problems, besides the fact that there are many visual estimations to be made regarding the coincidence of lines in the dials of the two capacitors.

Therefore a situation is faced wherein resources in constant development and progress as is the case with electronic circuits, are plagued by the inconveniences and problems caused by mechanical elements the essential characteristics of which have not changed in decades. The case of the standard capacitor is typical because they are now built with materials of excellent quality, they are solid and dependable but, never the less they are still mechanical instruments. Even so it is possible to build easily, as has just been described, oscillators that lead to permittivity values with four exact decimal figures and an error in the fifth. But it is also evident that the solution to these measurement problems lies in the totally electronic realm.

It is therefore evident that all these problems could be solved through totally electronic measuring devices and procedures.

In the case of the complex permittivity the automatization problem has been successfully dealt with through procedures that imply the frequency scan from the lower limit (even within the static region) up to well into the microwaves. So much so that for quite some time there exist commercial instruments of various origins and characteristics. However, unfortunately, with them it is not possible to achieve the sensitivity provided by static permittivity measurements.

This is the case of GB 2,306,660 that describes an electrical measuring apparatus and method to determine the presence of substantial amounts of decomposition products in break fluids through the complex permittivity method. The circuit disclosed in said patent provides a first value that depends on the imaginary part and a second value that depends on the real part of the permittivity. The oscillator allows for a periodic or continuous check and, through the volume of the frequency of an audible signal that can be incorporated into the circuit, the permittivity of the fluid is obtained. However, it is important to keep in mind that no measurement is made but a value is established as the result of a massive composition change due to the presence of decomposition products.

Another type of oscillator for the determination of complex permittivity in fluids is shown in U.S. Pat. No. 5,677,631, that discloses a coaxial two port waveguide flowline sensor, especially adapted to determine variables in fluids and their conditions in the case of high temperatures in drilling wells. Said sensor transmits radiofrequency signals, in the transverse electric mode (TEM), through well fluids that flow through the longitudinal cavity of a waveguide. Again, as in the previous case, the purpose is to establish substantial composition changes that do not require great sensitivity.

Furthermore DE 4,004,192 discloses an apparatus that measures variation in the permittivity of breaking fluids due to water content, with compensation of temperature variations. The device uses two measuring rings that are mounted on plastic to form a capacitor that uses the brake fluid as dielectric. In this fashion, by measuring the change in permittivity due to the presence of water it is possible to establish unacceptable levels of contamination. It also uses a resistor integrated to the sensor to compensate for temperature variations. Again only variations in the composition of the dielectric are established as a checking means and without great sensitivity.

Something similar can be seen in U.S. Pat No. 5,125,265 that discloses a contamination capacitance probe system comprising a capacitance to frequency converter, a frequency to voltage converter and a Schmidt trigger that provide a first and second control signals. The device of this invention is operable with two or more fluids of different permittivities that are either immiscible or miscible.

Regarding the circuit, U.S. Pat. No. 4,559,493 discloses an oscillating circuit for determining the purity of single or multi-component liquids (water and ink) from static permittivities using a cell linked to a multimeter and a frequency metter but with no temperature control.

Material moisture detection through static dielectric measurements with a cell and an RLC oscillatoing circuit is disclosed in U.S. Pat No. 4,782,282. Although exemplified for particulate solids the use in liquids is contemplated. However, again there is no reference to temperature control.

The choice of inductance values for the coil in the RLC oscillating circuit is mentioned in U.S. Pat. No. 3,319,209.

Somewhat similar is the circuit disclosed by U.S. Pat No. 3,793,585 for the continuous determination of single or multi-component liquids flowing through cell, through dielectric permittivity readings on a meter.

The same can be said of U.S. Pat Nos. 4,736,156 and 4,907,442 because they both refer to methods and systems for determining dielectric permittivity and capacitance to be used in the detection of moisture in liquids.

However, as already mentioned, none of the cited prior art indicates the need for an adequate and careful temperature control in the cell itself.

Evidently with any of these systems it would be impossible to determine continuously, with high sensitivity and precision, the presence of contaminants that, regardless of concentration, change only slightly the permittivity ($\in$) of the product.

Other attempts have been made to use static permittivity through frequency changes [i.e. A. Bonilla and B. Vasos, Journal of Chemical Education 54(2), 130 (1977) and R. Kurz, O. T. Anderson and B. R. Willeford, Jr., Journal of Chemical Education 54(3), 181 (1977)] the results, though interesting, were far from leading to a useful procedure to solve the problems of precision and sensitivity found in practical applications.

The problem to solve is then to find a device comprising an oscillator that will allow to measure the capacitance of a capacitor, used as cell, through the changes in frequency of the oscillator, in the static permittivity region without the need of standard and micrometric capacitors and with a strict temperature control in the cell. This implies to work at frequencies low enough so as not to be affected by relaxation phenomena, so that with a careful temperture control the static permittivity of liquids csn be determined in an automatic fashion, with sufficient sensitivity to detect the presence of contaminants having permittivities similar to that of the fluid or that are in small proportions, if of higher permittivity.

OBJECT OF THE INVENTION

Therefore, it is the object of this invention to provide a device comprising an RLC type circuit for the measurement of frequencies in the static region having an electronic oscillator connected to a carefully temperature controlled measuring cell through which a liquid flows, the permittivity of which is to be known.

Another object is to use a standard measuring cell without standard or micrometric capacitors with an adequate inductance and a monitored temperture control system.

Another object is to use a very stable oscillating circuit, the oscillating frequency of which can be held constant for sufficiently long periods of time so as to allow high precision measurements.

Another object is to use a rigid cell, of suitable dimensions, easy to connect and disconnect, and with an adequate temperature control. based on the use of a thermistor placed in a well drilled into the measuring cell wall.

Another object is that the cell has a sufficient electric capacitance to make high sensitivity measurements possible.

Another object is that the temperature control depends on an adequate thermostatization and constant monitoring of the temperature.

Another object is to obtain a procedure to determine the permittivity of a liquid placed in a measuring cell from the electric capacitance values calculated from the frequencies measured on the oscillator.

Another object is to obtain the permittivity directly from the frequency values measured on the empty and filled cell, taking previously into account the frequency value corresponding to the residual capacitance.

As hereabove described, the oscillating device and the procedure of the present invention are centered in the electronic device to determine absolute dielectric permittivities in real time and in a continuous manner with a high degree of sensitivity and precision and also on the constant monitoring and control of the temperature in the measuring cell. To achieve this it is necessary to obtain an electronic circuit of great stability, that operates within the frequency range where no relaxation phenomena occur, that is to say below 1 MHz and preferably between 10 and 200 kHz and the frequency changes of which are sufficiently large so as to ensure an adequate sensitivity of the measurements.

Strict and careful temperature control in the measuring cell is needed in view of the substantial dependence of the permittivity of liquids on the temperature. So much so that the old term dielectric constant was abandoned because its lack of constancy with, among other variables, the temperature in the measuring cell. As an example it may be cited that the permittivity of benzene changes by 0.002 units per degree centigrade [H. Bradford Thompson, Journal of Chemical Education, 43(2), 66–73 (1966)]. Therefore in order to obtain permittivity values with better than one 0.0001 units, necessary in precise control of the purity of liquids, a very strict control and temperture monitoring is necessary.

The invention will be better understood referring to the drawings, wherein: FIG. 1 shows the RLC oscillating circuit of the prior art used for static permittivity, wherein its capacitance is the result of three parallel capacitors: measuring cell, standard and micrometric capacitors [Review of Scientific Instruments, 65(4), 3067 (1996)].

DETAILED DESCRIPTION OF THE INVENTION

On the basis of the above arguments it is necessary to have a theoretical means to calculate, in a circuit, capacitance as a function of frequencies. This means exists and is none other than the known Thomson equation:

$$f = \frac{1}{2\pi\sqrt{LC}}$$

wherein f is the circuit oscillation frequency, L is its inductance and C the capacitance.

However, although the Thomson equation implies the calculation of capacitances that can be made simple by computational means, it introduces a source of error increasing the number of operations, something that has to be avoided.

The possibility to make these measurements automatically and in a continuous fashion requires an oscillator of great stability that can be connected to a frequency meter that has an RS232 port, in other words that can be connected to a computer.

The previously used circuit for static permittivity measurements did not allow continuous measurements because the substitution method used, made automation impossible as already described.

Figure 1:
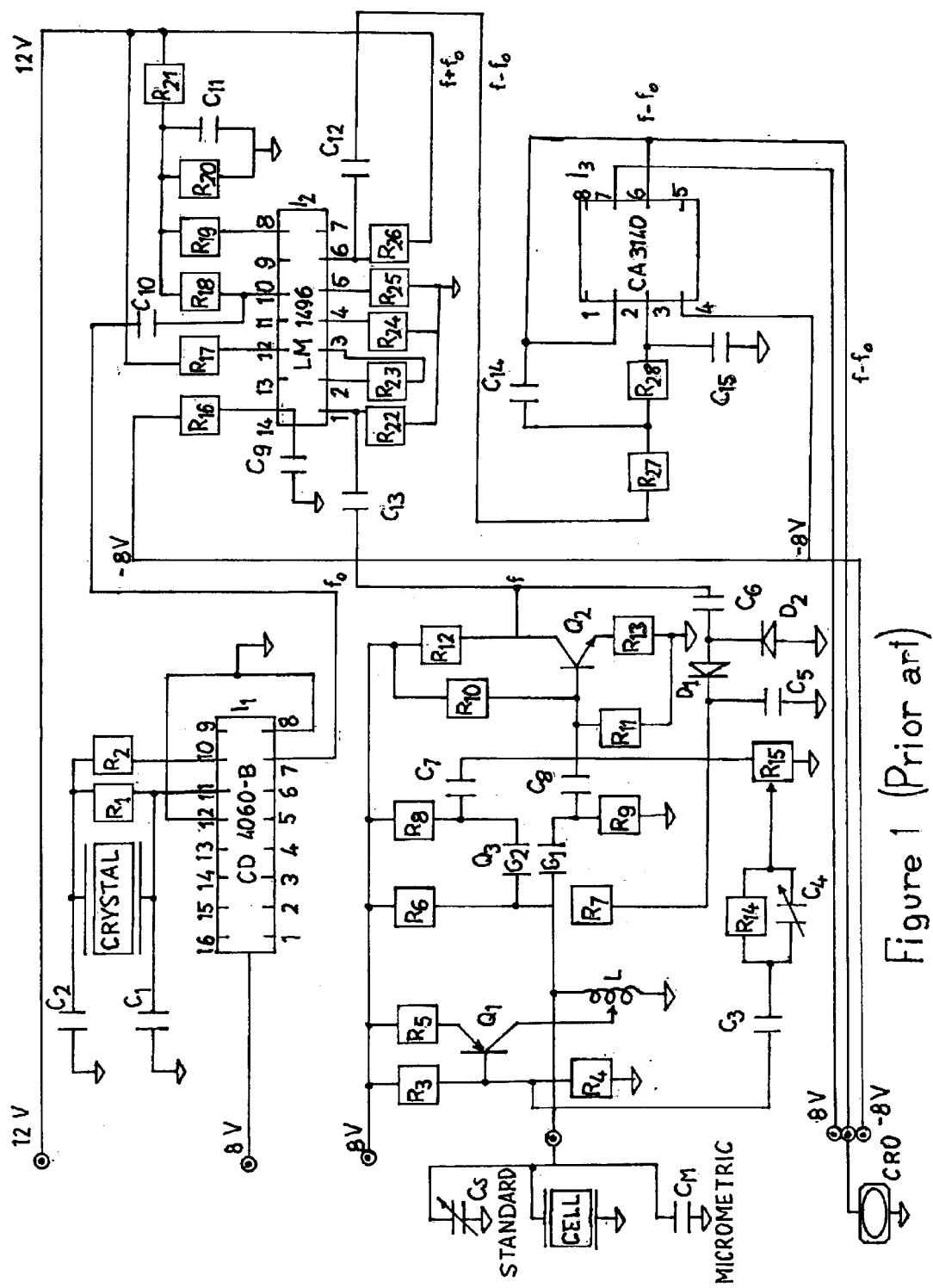

Numerous tests with a variety of circuit designs led to the Prior Art circuit described in FIG. 1. With it measurements of the static permittivity can be made continuously and without the described mechanical drawbacks. This circuit resulted from the examination of the capacitive part of the oscillator of FIG. 1, that is formed by the three already mentioned capacitors in parallel ($C_{cell}$, $C_{standard}$ and $C_{micrometric}$), because it was realized that if they were eliminated and the inductance L was suitably modified, the oscillator could be made to oscillate automatically within the desired frequency range. Namely between 10 and 200 kHz and preferably at 100±50 kHz. This new circuit is composed of the elements indicated in the following Table:

TABLE

Values for the circuit components

| No | Symbol | Component | Type |
|----|--------|-----------|------|
| 1  | B1     | Inductance |      |
| 2  | Q1     | Transistor Si | PNP 557 |
| 3  | Q2     | Transistor Si | NPN547 |
| 4  | Q3     | Double gate | 3N 201 |
| 5  | D1     | Diode Si Rf |      |
| 6  | D2     | BAY 45 Si |      |
| 7  | R1     | 10 kΩ     | 1.8 w |
| 8  | R2     | 39 kΩ     | 1.8 w |
| 9  | R3     | 3.3 kΩ    | 1.8 w |
| 10 | R4     | 22 kΩ     | 1.8 w |
| 11 | R5     | 10 kΩ     | 1.8 w |
| 12 | R6     | 470 kΩ    | 1.8 w |
| 13 | R7     | 510 kΩ    | 1.8 w |
| 14 | R8     | 82 kΩ     | 1.8 w |
| 15 | R9     | 22 kΩ     | 1.8 w |
| 16 | R10    | 2.2 kΩ    | 1.8 w |
| 17 | R11    | 1 kΩ      | 1.8 w |
| 18 | R12    | Trimmer   |      |
| 19 | R13    | Variable  |      |
| 20 | C1     | 0.1 µf 50 V |    |
| 21 | C2     | Variable  |      |
| 22 | C3     | 0.5 µf 50 V |    |
| 23 | C4     | 0.1 µf 50 V |    |
| 24 | C5     | 0.5 µf 50 V |    |

Figure 2:
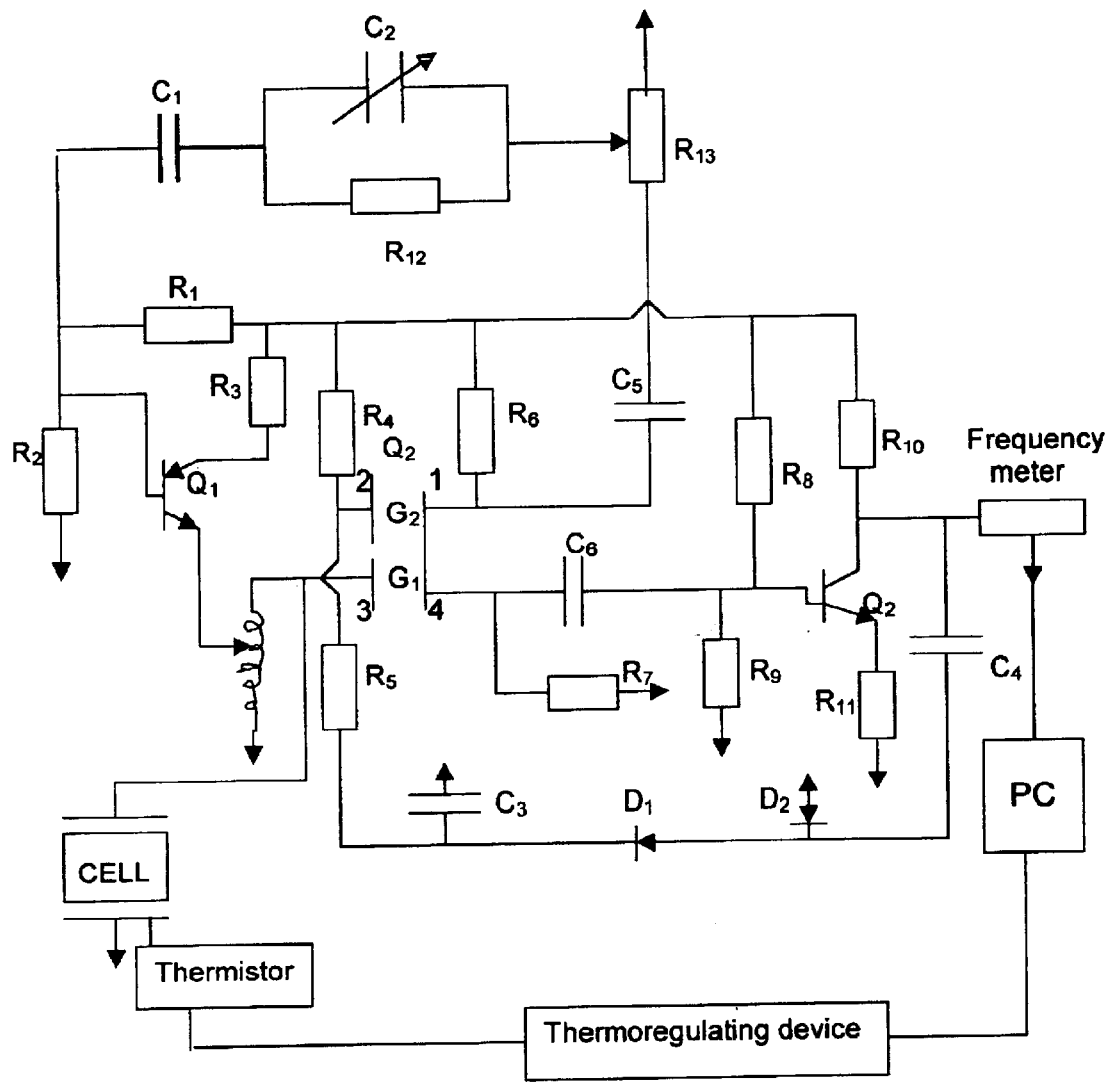
FIG. 2 shows the circuit of the present invention oscillator, that has no standard nor micrometric capacitors.

These elements are distributed on a printed circuit, according to the layout shown in FIG. 2. This printed circuit is obtained through standard procedures leading to the oscillator in the device of the present invention.

To obtain a frequency within the desired range, the main problem to solve is the value of inductance B1(Table 1) that has to be calculated as a function of the permittivities to be determined. This calculation can be done with the data found in any handbook of electronic components, like that provided by the Siemens company, Technical Descriptions and Characteristics for Students, 1986 Ed. (also later editions) pages 598 and ff. Since the majority of industrial liquids, with the exception of alcohols and aqueous solutions, such as hydrocarbons and chlorinated derivatives, esters, aliphatic and aromatic ethers and organic acids have permittivity values between 1.9 and 8 it is quite simple to estimate the necessary value for the inductance B1. In these cases it falls between 2.5 and 4.5 mH depending on the characteristics of both the nucleus and the wire winding. To this effect it was found that the most appropriate wires are those having a $3.1416\times10^{-4}$ mm$^2$ to $3.1416\times10^{-2}$ mm$^2$ section (or 0.01 to 0.1 mm dieameter) and that the nucleus can be either directly air or a ferromagnetic material like ferrite. The choice will depend on the desired size of the complete oscillator since in both cases the frequency stability achieved is quite similar in both cases.

Therefore to obtain the oscillator a printed circuit is built through customary techniques, as previously indicated, and the plate is placed in a metallic box with some insulating material on the walls, to avoid sudden temperature changes in the inside. An 8 V power source is needed, that for convenience can be place outside the box. This box has three connectors: two are BNC connectors, one for a rigid connection to the cell and the other to supply data to the frequency meter and the third is a simple connector that links the thermistor to the multimeter and thermoregulator.

Figure 4:
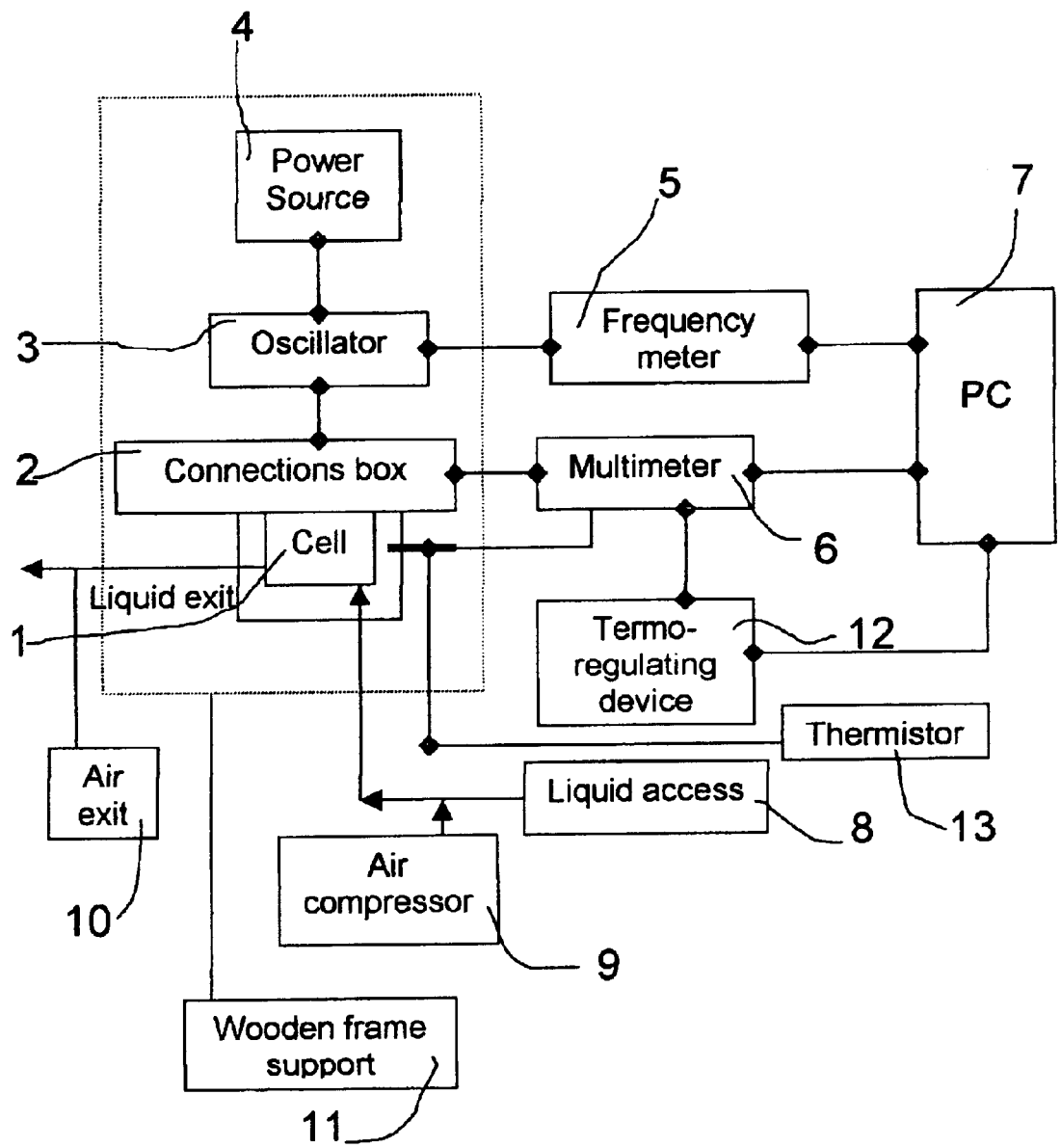
FIG. 4 shows a layout of the connections between the different components used for the determination of the dielectric permittivity of a liquid.

FIG. 4 shows where the individual components are placed.

Under these conditions an oscillator can be obtained with an oscillating frequency between 150 and 200 kHz, with frequency changes that do not exceed 2 Hz over a period of several hours of continuous operation.

To calculate the permittivity a set of equations is used that are the result of the following reasoning:

As above indicated, the permittivity is the result of the division of capacitances $\in = C_f/C_e$, wherein it is necessary to introduce the residual capacitance that corresponds to everything that is not strictly part of the measuring cell (dead spaces, connections, cables) and that can be indicated as $C_r$. So that the above equation becomes:

$$\in = C_f - C_r/C_e - C_r$$

now then, each of these capacitance values can be converted into the corresponding frequency value by means of the already indicated Thomson equation so that, considering $\in_s$ as the permittivity of the standard compound used to determine the residual capacitance the final equation becomes:

$$\varepsilon = \frac{\frac{1}{4\pi^2 f_f^2 L} - \frac{1}{(\varepsilon_s - 1)}\left(\frac{\varepsilon_s}{4\pi^2 f_{es}^2 L} - \frac{1}{4\pi^2 f_{fs}^2 L}\right)}{\frac{1}{4\pi^2 f_e^2 L} - \frac{1}{(\varepsilon_s - 1)}\left(\frac{\varepsilon_s}{4\pi^2 f_{es}^2 L} - \frac{1}{4\pi^2 f_{fs}^2 L}\right)}$$

Wherein it can be seen that the inductance values can be simplified, leaving a much simpler equation that only contains the frequency values corresponding to the filled and empty cell and the permittivity of the standard (subindices f, e and s) used to determine the residual capacitance, that becomes then a constant of the procedure. For this purpose benzene ($\in=2.2727$) and carbon tetrachloride ($\in=2.2276$) are generally used.

$$\varepsilon = \frac{\frac{1}{f_f^2} - \frac{1}{(\varepsilon_s - 1)}\left(\frac{\varepsilon_s}{f_{es}^2} - \frac{1}{f_{fs}^2}\right)}{\frac{1}{f_e^2} - \frac{1}{(\varepsilon_s - 1)}\left(\frac{\varepsilon_s}{f_{es}^2} - \frac{1}{f_{fs}^2}\right)}$$

Evidently, all calculations required by this equation can be implemented on a computer without any difficulties.

To determine the permittivity of a flowing liquid it is necessary to resort to a capacitor with two or more parallel plates. These can be planar or cylindrical, with sufficient distance between them so that the flow is steady and, even if relatively fast, does not cause any temperature changes due to friction on the walls.

In the case of the planar capacitors, the most adequate geometry is that of a rectangle, while if cylindrical the components have to be coaxial. In both cases the separation between plates must not surpass 5 mm, because larger values lead to retention of air bubbles and also would lead to an increase in the overall measuring cell dimensions, in view of the large capacitance required for sensitive measurements. On the other hand the lower limit is 0.5 mm because otherwise the flow would be two slow. In the former case capacitance would decrease appreciably making it necessary to increase dimensions beyond what is reasonable and practical, while in the latter case there would be necessarily undesirable frictions.

Anyway the adequate dimensions of the cell acting capacitor can be quite approximately calculated considering that there exist equations, well tested experimentally, that allow to calculate the capacitance of capacitors of the most diverse geometries. These equations can be found in handbooks such as the HANDBOOK OF CHEMISTRY AND PHYSICS, published yearly by The Chemical Rubber Co. of the U.S. and that exist in every physics and chemistry laboratory.

Specifically for a planar capacitor the equation used is $$C = \frac{\varepsilon A}{d}$$

While for a cylindrical one it is $$C = \frac{\varepsilon A}{4\pi d}$$

Wherein C is the capacitance, $\in$ is the permittivity of the dielectric that can be taken as air and equal to unity, A is the plate surface and d the distance between the plates.

As a result the dimensions will depend on the capacitances that are to be measured. To this effect prior experience has shown that for high sensitivity measurements in liquids with permittivities between 1.9 and 8, capacitances between 20 and 200 picoFarads are required.

Considering now that the most adequate frequency range lies between 80 and 200 kHz, as calculated with the previously indicated inductance values (2.5 to 4.5 mH) and the electric capacitance needed to obtain permittivity values in the desired range with the necessary sensitivity and precision, it is quite simple to calculate the dimensions of the measuring cell regarding plate surface and separation between the plates.

Figure 3:
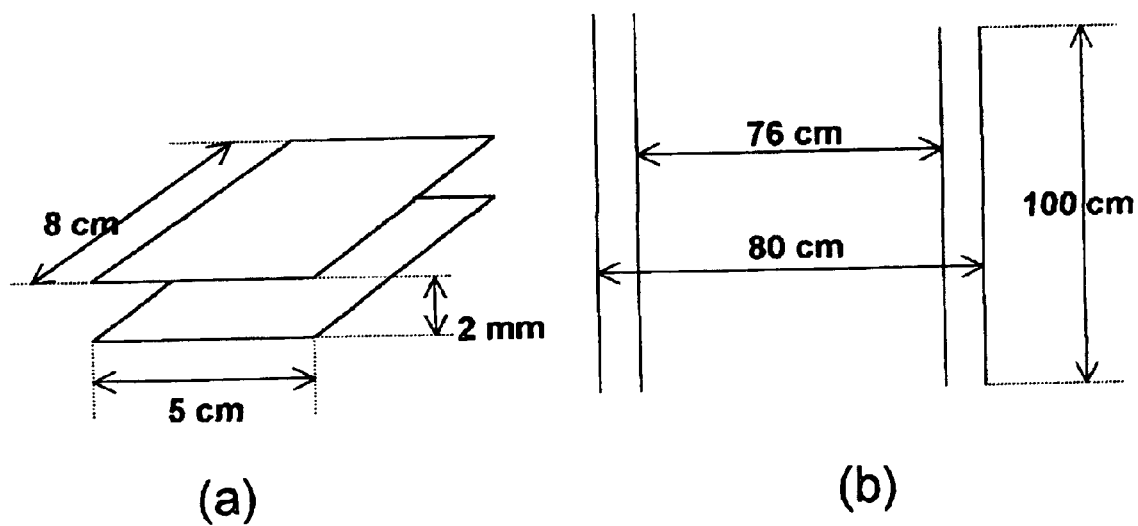
FIG. 3 show different measuring cell structures: for plane parallel plates (A), for two coaxial cylinders (B) and three coaxial cylinders (C)

Thus for instance, an oscillation frequency of 100 kz requires and inductance of 4 mH, that according to the Thomson equation indicates a capacitance of 200 picoFarads. Then, to achieve this value in a planar capacitor with a plate separation of 2 mm, that is adequate for a good steady flow, a 40 cm² plate surface is necessary and the most convenient dimensions (length and breadth) would be 8 and 5 cm respectively (FIG. 3a). Although this could be an ideal situation, the construction of such a cell carries substantial difficulties making preferable a cell of cylindrical geometry. For these there is enough experience to develop a design of adequate size and shape.

On the other hand for a cylindrical capacitor, with the same plate separation, to coaxial cylinders are required having 7.6 and 8 cm of outer and inner diameter respectively and are 10 cm high (FIG. 3b). In the case of cylindrical cells and low viscosity liquids it is also possible to consider a structure of three coaxial cylinders thus increasing the electric capacitance of the cell and obtaining a substantial reduction in the plate size, as indicated in FIG. 3c.

Figure 3C:
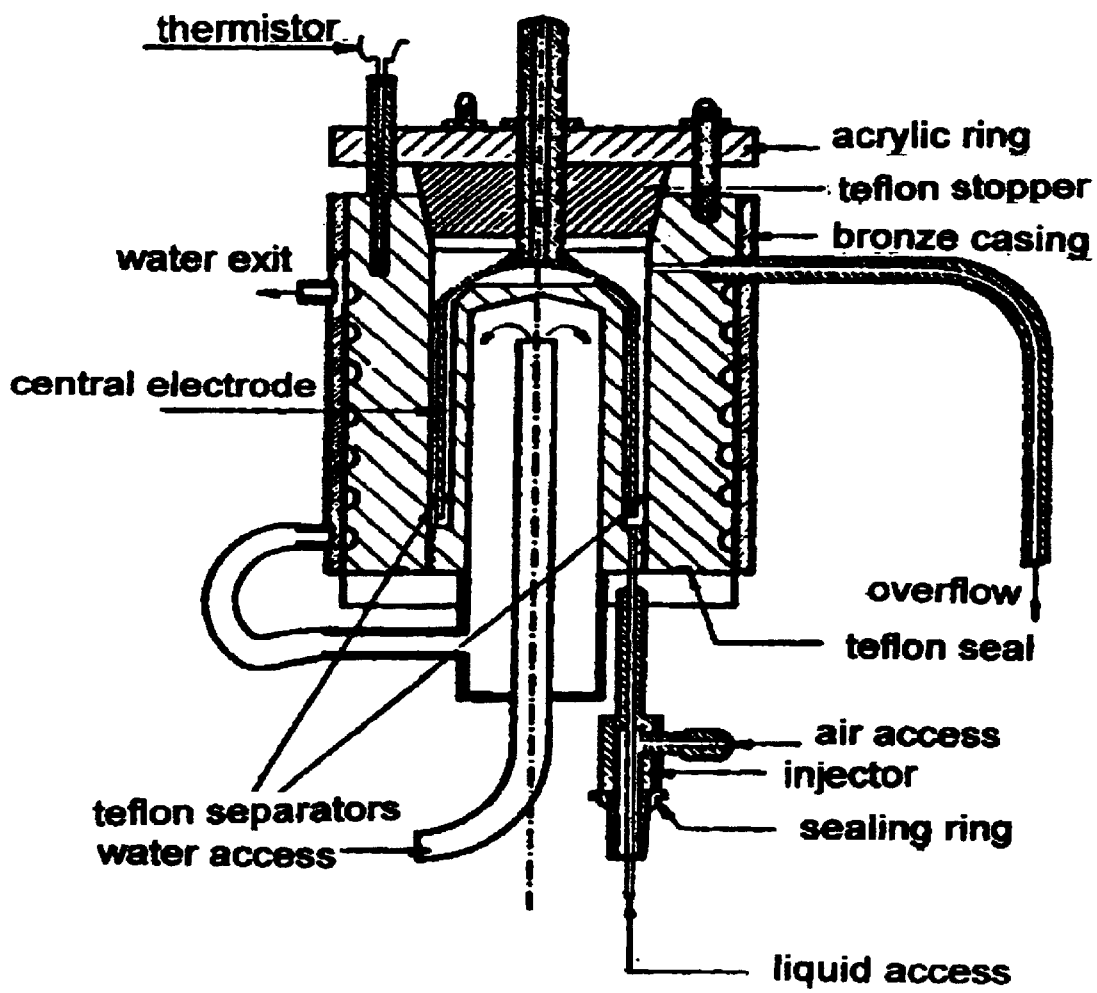

The following are some permittivity values obtained with the three coaxial cylinder cell shown in FIG. 3c.

| | Permittivity | | |
|---|---|---|---|
| | $CCl_4$ | Benzene | Toluene |
| 298.15K | 2.2279 | 2.2782 | 2.3800 |
| 303.15K | 2.2179 | 2.2677 | 2.3690 |
| 308.15K | 2.2079 | 2.2565 | 2.3558 |

In FIG. 4 the placement of the measuring cell 1 can be seen in the flow diagram. This cell 1 is a two component cylindrical coaxial cell that is connected through a connection box 2 to the oscillator circuit 3, indicating the measured value. The oscillator is in turn connected to a power source 4 and a frequency meter 5. The connection box 2 communicates with a multimeter 6 for temperature reading and control, that together with the frequency meter 5 communicates with a computer 7 that determines, in a continuous fashion, automatically and in real time, the dielectric permittivity value of the liquid that flows through the parallel plates of the measuring cell 1 and controls the temperature, through readings by the multimeter 6. Access of the fluid 8 to the measuring device is achieved through compressed air from a compressor 9, that causes the liquid to enter. At the cell exit, the liquid continues to flow generating the air flow 10. The whole measuring device is placed on a wooden frame 11 support. The cell temperature is controlled with a thermistor 12 placed in a well drilled in the wall of the measuring cell 1, by reading with the multimeter 6 and regulated by a themoregulating device 13 to which it is linked and connected to the computer 7 for monitoring and control.

The procedure to determine the static dielectric permittivity of a liquid of the present invention comprises the steps of:
- determining the value of the inductance needed for the circuit of the present invention so that it generates an oscillation frequency of values within the range of 50 and 200 kHz,
- determining section of the wires and the type of nucleus to be used in the inductance depending on the value found,
- determining the needed capacitance value for the measuring cell so that both empty and filled the circuit will oscillate within the desired frequency range,
- determining the residual capacitance of the device using a suitable standard liquid,
- adjusting the cell temperature through an appropriate thermoregulating system or measuring with a thermistor placed in the cell, the cell temperature both empty and filled,
- making the liquid flow through the cell,
- recording the cell temperature once it has reached thermal equilibrium, and keeping it steady through the thermoregulating device,
- recording the frequency values of the cell both empty and filled, through the computer connected frequency meter,
- establishing the permittivity value of the fluid in real time through computer calculations with a previously uploaded program, and
- comparing, with the uploaded program, the degree of coincidence of the determined permittivity with that expected that was previously stored.

The invention has been described and shown with reference to particular embodiments, but variations within the spirit and scope of the general inventive concept will be apparent to those skilled in the art. For example, impedance values, cell sizes and capacitances and even frequency ranges can be changed to accomodate different permittivity values without departed from the general inventive concept. Accordingly it should be clearly understood that the form of the invention as described and depicted in the specification and drawings is illustrative only, and is not intended to limit the scope of the invention. All changes which come within the meaning and range of the equivalence of the claims are therefore intended to be embraced therein.

What I claim as my invention is:

1. An instrument to determine, in a continuous manner, the purity of single or multi-component liquids from the static dielectric permittivity in the region of static permittivity, related to an oscillating circuit connected to measuring cell through which the liquid to be examined for purity flows, which comprises that in the absence of standard and micrometric capacitors, said measuring cell has a capacitance in vacuum of between 150 and 200 pF, linked to said oscillating circuit through a connection box that is linked to said circuit through an inductance previously determined as a function of the permittivities to be determined, the section of the wires of which is approximately $3.1416 \times 10^{-4}$ mm$^2$ to $3.1416 \times 10^{-2}$ mm$^2$, or 0.01 to 0.1 mm in diameter and its nucleus is of air or of a ferromagnetic material, characterized in that it comprises a thermistor linked to a multimeter and in turn said cell connected to a thermoregulating device for temperature control.

2. The instrument of claim 1, characterized in that said multimeter, and thermoregulating device are connected to a computer.

3. A measuring procedure for the determination of the electric permittivity of single or multi-component liquids using the oscillating circuit of claim 1, characterized in that it comprises the steps of:
- determining the inductance value needed for the circuit of the present invention so that it generates an oscillation frequency of values between 10 and 200 kHz,
- determining the wire sections and the nature of the nucleus to be used in the inductance in agreement to the value found,
- determining the measuring cell capacitance value needed so that both when empty and filled, the circuit is made to oscillate within the desired frequency range, characterized in that it comprises the steps of:
- determining the residual capacitance of the cell through the use of an adequate liquid standard,
- adjusting the cell temperature by means of a thermoregulating device or by determining, through measurement with a thermistor placed in the cell, the temperature of said cell both empty and filled,
- having the liquid flow through the cell, recording the frequency values of both the empty and filled cell with a frequency meter connected to a computer,
- establishing the permittivity value of the fluid in real time through the calculations performed by the computer by means of a previously uploaded program and,
- comparing, through the uploaded program, the degree of coincidence of the determined permittivity with that expected as compared with the previously stored permittivity values.

* * * * *